(12) United States Patent
Shareef et al.

(10) Patent No.: US 7,285,425 B2
(45) Date of Patent: Oct. 23, 2007

(54) ASSAY TEST SYSTEM FOR REGULATING TEMPERATURE

(75) Inventors: Nazeer H. Shareef, North Attleboro, MA (US); James E. Smous, Elkhart, IN (US); James P. Albarella, Granger, IN (US)

(73) Assignee: Siemens Medical Solutions Diagnostics, Tarrytown, NY (US)

( * ) Notice: Subject to any disclaimer, the term of this patent is extended or adjusted under 35 U.S.C. 154(b) by 305 days.

(21) Appl. No.: 10/475,871

(22) PCT Filed: May 14, 2002

(86) PCT No.: PCT/IB02/01652

§ 371 (c)(1),
(2), (4) Date: Oct. 22, 2003

(87) PCT Pub. No.: WO02/093169

PCT Pub. Date: Nov. 21, 2002

(65) Prior Publication Data

US 2004/0115832 A1    Jun. 17, 2004

(51) Int. Cl.
*G01N 33/558* (2006.01)
(52) U.S. Cl. .................. 436/514; 422/56; 422/58; 435/287.1; 435/287.2; 435/287.7; 435/805; 435/810; 435/970; 436/810
(58) Field of Classification Search .................. None
See application file for complete search history.

(56) References Cited

U.S. PATENT DOCUMENTS

| | | | |
|---|---|---|---|
| 3,261,668 A | 7/1966 | Natelson | |
| 4,584,275 A | 4/1986 | Okano et al. | |
| 4,847,470 A | 7/1989 | Bakke | |
| 5,110,552 A | 5/1992 | Guigan | |
| 5,137,808 A | 8/1992 | Ullman et al. | |
| 5,143,084 A | 9/1992 | Macemon et al. | |
| 5,147,609 A | 9/1992 | Grenner | |
| 5,171,533 A | 12/1992 | Fine et al. | |
| 5,188,963 A | 2/1993 | Stapleton | |
| 5,215,718 A | 6/1993 | Katzer et al. | |
| 5,221,448 A | 6/1993 | Weinberger et al. | |
| 5,223,219 A | 6/1993 | Subramanian et al. | |
| 5,230,866 A | 7/1993 | Shartle et al. | |
| 5,232,667 A | 8/1993 | Hieb et al. | |
| 5,344,754 A * | 9/1994 | Zweig | 435/4 |

(Continued)

FOREIGN PATENT DOCUMENTS

| | | |
|---|---|---|
| EP | 0288793 A2 | 11/1988 |
| EP | 0397424 A2 | 11/1990 |
| EP | 0402588 A2 | 12/1990 |
| EP | 0878538 A2 | 11/1998 |
| WO | WO9107486 | 5/1991 |
| WO | WO93/19207 A1 | 9/1993 |

*Primary Examiner*—Christopher L. Chin
(74) *Attorney, Agent, or Firm*—Harold Wells, Esq.

(57) ABSTRACT

A device for evaluating at least one analyte in a test sample. The device comprises a cassette having a hollow test chamber, a test strip disposed within the test chamber for receiving the test sample, and a temperature control member. The cassette has at least one aperture extending from an exterior of the cassette to the hollow test chamber. The test strip includes a reagent adapted to react with the at least one analyte to produce a reaction indicative of the presence of the analyte. The temperature control member is adapted to extend through the at least one aperture in the cassette and into the test chamber for controlling the temperature of the test chamber.

28 Claims, 4 Drawing Sheets

U.S. PATENT DOCUMENTS

| | | | |
|---|---|---|---|
| 5,554,531 A * | 9/1996 | Zweig | 435/286.1 |
| 5,653,243 A | 8/1997 | Lauks et al. | |
| 5,714,390 A | 2/1998 | Hallowitz et al. | |
| 6,197,494 B1 | 3/2001 | Oberhardt | |
| 6,338,969 B1 | 1/2002 | Shareef et al. | |

* cited by examiner

ASSAY TEST SYSTEM FOR REGULATING TEMPERATURE

FIELD OF THE INVENTION

The present invention relates generally to the field of qualitative and semi-qualitative assays, and more particularly to a cassette for regulating the temperature for an assay.

BACKGROUND OF THE INVENTION

Immunochromatographic strip formats have become increasingly popular for qualitative and semi-quantitative assays which use visual detection schemes. This type of assay involves the application of a liquid test sample suspected of containing an analyte to be detected to an application zone of an immunochromatographic test strip. The strip is comprised of a matrix of absorbent material through which the test fluid and reagents for detecting the analyte can flow by capillarity from the strip's application zone to a capture zone where a detectable signal, or the absence thereof, reveals the presence of the analyte. Typically, the strip will include means for immunospecifically binding the analyte to be detected with its specific binding partner which bears the detectable label. In one such scheme, the strip contains an enzyme-labeled, mobile binding partner for the analyte which is located in a zone downstream from the sample application zone. If analyte is present in the test sample, it will combine with its labeled binding partner to form a complex which will flow along the strip to a detection zone which contains a substrate for the enzyme label which is capable of providing a colored response in the presence of the enzyme. The strip may contain a zone in which the analyte is immobilized, so that a labeled binding partner which does not combine with analyte, due to the absence of analyte in the sample, will be captured and thereby inhibited from reaching the detection zone. There have been various modifications of this technique, all of which involve some competitive specific binding system in which the presence or absence of analyte in the test sample is determined by the detection or lack thereof of labeled binding partner in the detection zone.

An alternative to the above described immunometric assay which detects the free-labeled binding partner is the so-called sandwich format in which the capture zone contains immobilized antibodies against an epitope of the analyte which is different from the epitope to which the labeled antibody is specific. In this format, the analyte is sandwiched between the immobilized and labeled specific binding partners, and it is therefore an immunometric assay which detects the bound, labeled specific binding partner.

Not all of the schemes for immunochromatography rely on an enzyme-labeled binding partner/enzyme substrate for providing the signal for detection of the analyte. For example, U.S. Pat. No. 4,806,311 discloses a multizone test device for the specific binding assay determination of an analyte and an immobilized binding partner therefor together with a capture zone for receiving labeled reagent which migrates thereto from the reagent zone. The capture zone contains an immobilized form of a binding substance for the labeled reagent. The labeled reagent bears a chemical group having a detectable physical property, so that it does not require a chemical reaction with another substance in order to be detected. Exemplary of such groups are species of fluorescers, phosphorescent molecules, radioisotopes and electroactive moieties.

U.S. Pat. No. 4,703,017 describes the use of visible particulate labels for the receptor. Various particulate labels such as gold sol particles and visible dye containing liposomes are mentioned. PCT Patent Application Publication No. WO 96/34271 discloses a device for determining a target analyte and creatinine in a fluid test sample. The device has an assay strip for the detection of creatinine and a second assay strip for the detection of the target analyte. The creatinine concentration can be determined colorimetrically or by the specific capture of labeled creatinine binding partners. The concentration of the target analyte is corrected based on the sample's creatinine concentration which correction can either be done manually or by means of a properly programmed reflectance analyzer.

Immunochromatographic strip formats provide a viable system for the determination of various analytes (whether they be antigens or antibodies) but suffer from the limitation that they yield results which are at best semi-quantitative when, for some analytes, more precise, quantitative results are required. The strip can be prepared from any matrix material through which the test fluid carrying the analyte and labeled binder-analyte contained therein can flow by capillarity; the matrix can be of a material which is capable of supporting non-bibulous lateral flow, described in U.S. Pat. No. 4,943,522 as liquid flow in which all of the dissolved or dispersed components of the liquid are carried through the matrix at substantially equal rates and with relatively unimpaired flow as contrasted to preferential retention of one or more components as would be the case if the matrix material were capable of absorbing or imbibing one or more of the components. An example of such matrix material is the high density or ultra high molecular weight polyethylene sheet material from Porex Technologies of Fairburn, Ga. Equally suitable for use as the matrix from which the chromatographic strip can be fabricated are bibulous materials such as paper, nitrocellulose, and nylon.

One variable which needs to be controlled in analyses using immunochromatographic strips is temperature control. Temperature is an important variable because all immunochemical reactions are characterized by two temperature-dependent opposite reactions at the same time. These are the formation of an immune complex from an antigen and its antibody and the appearance of free antigen and antibody by dissociation of the immuno complex. Increasing the temperature increases the rate of reaction, and because immunochromatographic strip formats are usually measured under nonequilibrium conditions due to the short assay times involved, temperature control, both within and between laboratories, is critical for insuring consistent reaction rates thereby providing more reproducible assay quantitation. Currently, temperature is not controlled. Typically immunochromatographic strips are run at ambient temperatures which can range from 20-30° Centigrade. Because reaction rates approximately double for every 10 degree centigrade increase in temperature, it is apparent that controlling temperature allows for control of the immunochemical reaction thereby leading to more reproducible results.

Devices for controlling the temperature of an assay include a disposable test cassette having a thermally conductive member, such as an aluminum bar, disposed within the cassette. In such a device, the thermally conductive bar is in thermal communication with the test strip for regulating the temperature of the assay. The thermally conductive bar accelerates the warning of the assay during an incubation period. After the assay is completed, the cassette including the thermally conductive member is discarded. These devices have achieved good results in controlling the temperature of an assay. However, one drawback associated with such a device is that the thermally conductive member is discarded along with the disposable test cassette having the thermally conductive member disposed therein. Therefore, the costs associated with providing the thermally conductive member are incurred with each use of the disposable test cassette having a thermally conductive member disposed therein. Accordingly, there is a need for a low-cost, easily manufacturable test cassette for controlling the temperature of an assay.

SUMMARY OF THE INVENTION

A device for evaluating at least one analyte in a test sample comprises a cassette having a hollow test chamber, a test strip disposed within the test chamber for receiving the test sample, and temperature control member. The cassette has at least one aperture extending from an exterior of the cassette to the hollow test chamber. The test strip includes a reagent adapted to react with the analyte to produce a reaction indicative of the presence of the analyte. The temperature control member is adapted to extend through the aperture in the cassette and into the test chamber for controlling the temperature of the test chamber.

The above summary of the present invention is not intended to represent each embodiment, or every aspect, of the present invention. Additional features and benefits of the present invention will become apparent from the detailed description, figures, and claims set forth below.

BRIEF DESCRIPTION OF THE FIGURES

Other objects and advantages of the invention will become apparent upon reading the following detailed description in conjunction with the drawings in which.

DETAILED DESCRIPTION OF THE ILLUSTRATED EMBODIMENTS

As discussed in the background section, devices for controlling the temperature of an assay include a disposable test cassette including a thermally conductive member, such as an aluminum bar, disposed within the cassette. The thermally conductive member facilitates the temperature control of the assay. However, a drawback associated with such a device is that the thermally conductive member is discarded along with the disposable test cassette having the thermally conductive member disposed therein.

The present invention provides a low-cost, easily manufacturable test cassette which allows a heating element to protrude into a test chamber of the cassette to control the temperature of an assay. The present invention eliminates the need for a separate temperature control member, such as the above-mentioned aluminum bar, to be disposed within the test cassette and is discarded with the test cassette after the assay. As mentioned above, more accurate results can be obtained from the assay when the temperature of the assay is controlled.

Figure 1:
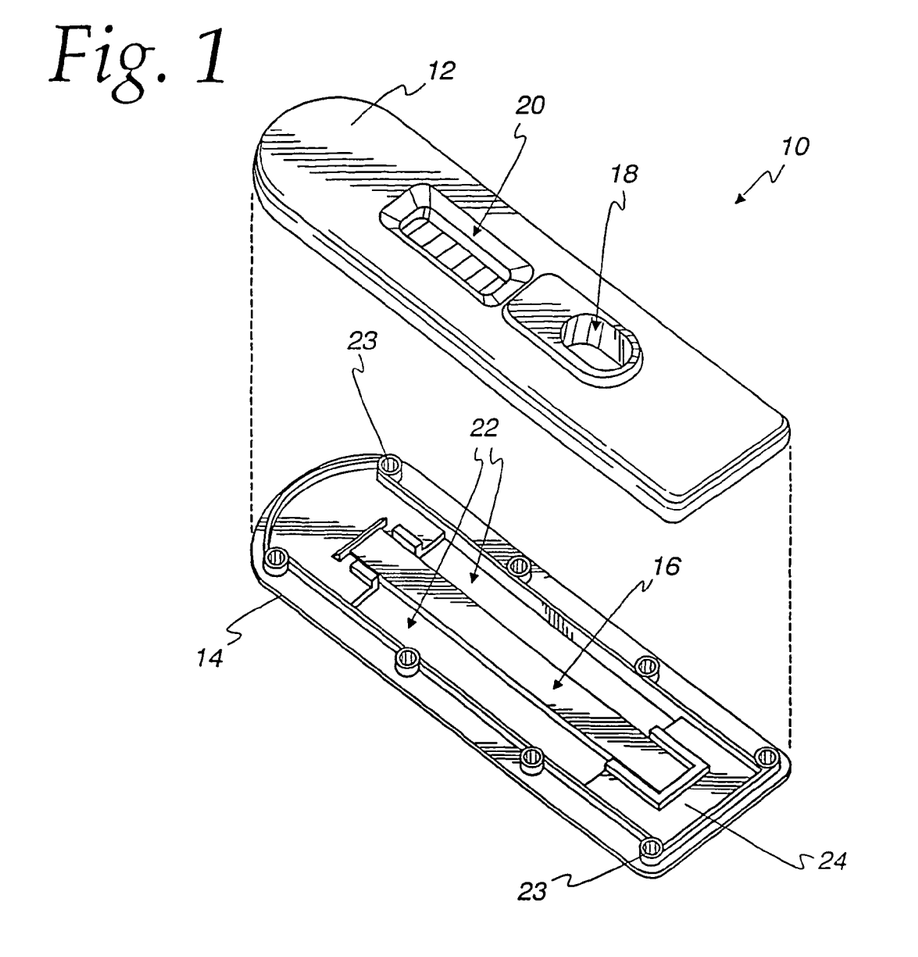
FIG. 1 is a perspective view of a top and a bottom portion of cassette according to one embodiment of the present invention.

Referring initially to FIG. 1, an assay test cassette 10 according to one embodiment of the present invention is shown. The test cassette 10 includes a cassette top 12 and a cassette bottom 14 that are designed to mate with one another after a test strip (not shown), such as a immunochromatographic test strip, has been placed into a test strip receiving well 16 of the cassette bottom 14.

The cassette top 10 has an application port 18 through which the liquid test sample is applied to the test strip and a viewing port 20 through which the detection zone of the test strip can be viewed. The cassette may optionally include slits (not shown) for venting purposes. The cassette top 12 and bottom 14 are fabricated to form a hollow test chamber when mated. Before mating, a test strip is placed in the test strip receiving well 16. The cassette 10 is designed so that the application region of the test strip (which may be the first region containing the labeled specific binding agent or a separate region of the strip) is aligned with the sample application port 18 and the detection region of the strip is aligned with the viewing port 20 when the top 12 and bottom 14 of the cassette are mated.

The cassette bottom 14 includes a pair of rectangular-shaped apertures or slots 22 through which temperature controlling elements protrude into the hollow test chamber of the cassette 10, when the cassette top 12 and bottom 14 are mated, for regulating the temperate of an assay. The cassette bottom 14 can be equipped with a series of sockets 23 which lock up with pins (not shown) in the cassette top 12 when the cassette top 12 and bottom 14 are mated, to hold the top 12 and bottom 14 snugly together. The cassette bottom optionally includes a depression 24 to hold a desiccant.

Various immunochromatographic strip formats are suitable for use in the present invention. The strip typically has a first region (e.g., a reagent pad) that is made of an absorbent material such as paper or a membrane that has been impregnated with a reagent associated with a particular test to be performed. In conventional immunochromatographic devices, the strip is then placed into the well 16 of the cassette bottom 14 so that the reagent pad is located under the sample application port 18. Alternatively, the strip can have an application zone that is free of the reagent with the reagent region being downstream and in liquid communication therewith. Such a test strip is disclosed in U.S. Pat. No. 4,446,232.

Figure 2:
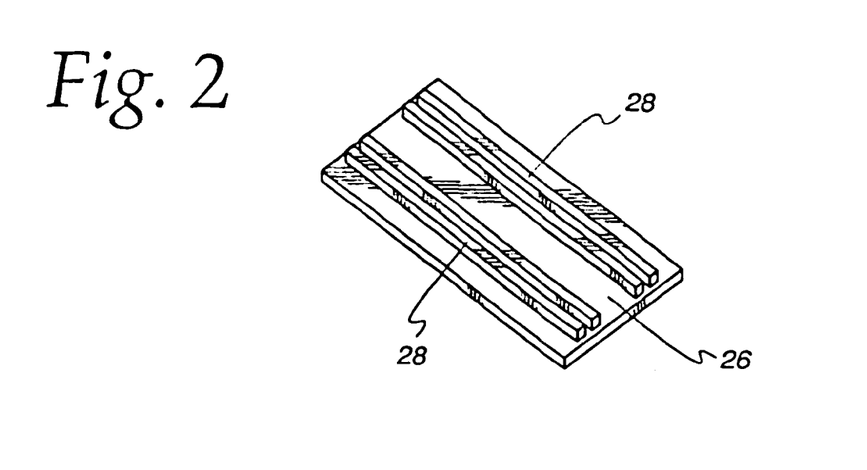
FIG. 2 is a perspective view of a fixture plate having fins according to one embodiment of the present invention.

Referring to FIG. 2, a fixture plate 26 having integral fins 28 is shown for providing temperature control to the test cassette 10 during an assay. The fixture plate 26 and fins 28 are fabricated such that the fins 28 constitute an integral part of the fixture plate 26. By integrally manufacturing the fixture plate 26 and fins 28, heat loss from the interfaces between the plate 26 and the fins 28 is mitigated. Put another way, the overall thermal conductivity of the fixture plate and fins would be reduced at the interface between the fins and fixture plate if the fins were connected to the fixture plate with, for example, screws, instead of being integrally formed. The fixture plate 26 and fins 28 can be made out of any thermally conductive material which is more thermally conductive than the cassette 10. (The cassette 10 is made of plastic according to one embodiment of the present invention.) Thermally conductive materials for the plate 26 and fins 28 include copper, gold, silver, aluminum, and other alloys with superior thermal properties. In one embodiment of the present invention, the fixture plate 26 and fins 28 are made out of aluminum. Aluminum is an excellent thermal conductor and is relatively low in cost in comparison to gold, silver, and copper.

Figure 3:
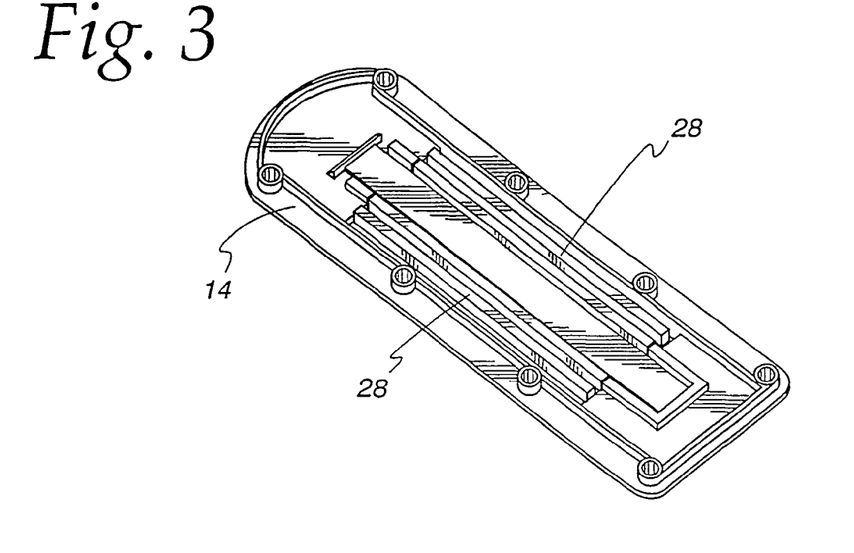
FIG. 3 is a perspective view of a bottom portion of a cassette upon a fixture plate having fins according to one embodiment of the present invention.

Referring to FIG. 3, the cassette bottom 14 is shown laid upon the fixture plate 26 such that the fins 28 protrude through the slots 22 disposed within the cassette bottom 14. When the cassette top 12 and bottom 14 are mated, the fins 28 extend up into the hollow test chamber of the cassette 10 to provide temperature control to the test chamber which contains the immunochromatographic test strip at the time of an assay.

Figure 4:
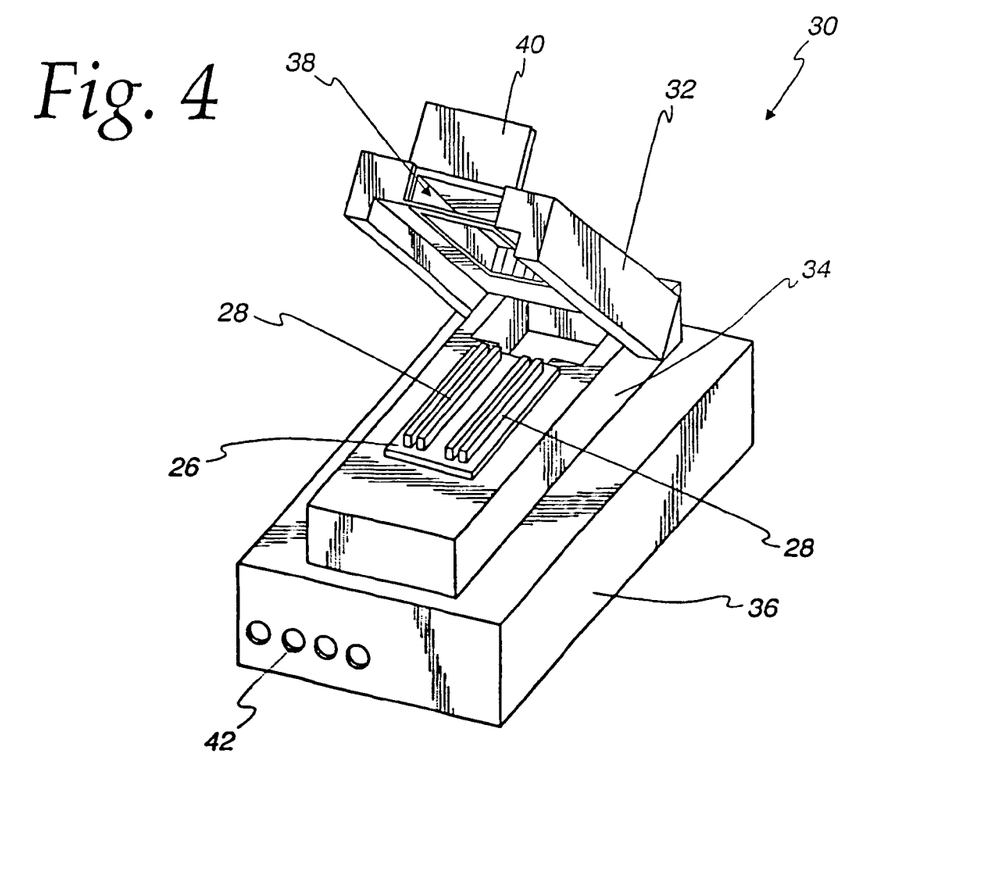
FIG. 4 is a perspective view of a temperature control mechanism according to one embodiment of the present invention.

Referring to FIG. 4, a temperature control mechanism 30 is shown. The temperature control mechanism 30 includes a cassette carrier 32, a fixture carrier or heating device 34, and a circuit box 36. The cassette carrier 32 is hingedly connected to the heating device 34 allowing a cassette 10 placed within the cassette carrier 32 to be rotated downward thus bringing the cassette bottom 14 into contact with the fixture plate 26 which is disposed on the heating device 34. When the assay is conducted, a cassette 10 having a test strip disposed therein is inserted into the cassette carrier 32 through an opening 38 of the cassette carrier 32. After the cassette 10 is inserted into the carrier 32, a door 40 of the cassette carrier 32 is closed to retain the heat generated within the enclosed space of the cassette carrier 32. The cassette carrier 32 is then rotated downward.

The fixture plate 26 having integral fins 28 is thermally coupled to the heating device 34. Thus, the fixture plate 26 and the fins 28 are heated by the heating device 34 by way of conduction. The heating device 34 comprises a thermoelectric device such as, for example, a Peltier Effect thermoelectric device. The circuit box 36 contains the necessary electronics to provide power to and to control the electric heating element of the heating device 34 and optionally includes one or more light emitting diodes 42 ("LEDs") which provide a visual indication of the operational status of the mechanism 30.

When the cassette carrier is closed (e.g., downwardly rotated), the cassette bottom 14 is brought into contact with the fixture plate 26 causing the fins 28 to protrude through the slots into the hollow test chamber. The fins 28, in turn, heat the test chamber thus regulating the temperature of the reaction. Tension coil springs (not shown) between the cassette carrier 32 and the fixture carrier 34 maintain contact between the cassette bottom 14 and the fixture plate 26.

In operation, a test strip is placed in the well 16 of the cassette bottom 14 which is then mated with the cassette top 12. A fluid test sample (e.g., urine) is applied to the first region of the test strip or optional sample application pad. The fluid test sample flows through the first zone of the strip the fluid test sample and contacts the labeled antibodies which flow along with the fluid test sample towards the detection zone. At the detection zone the labeled antibodies are captured either by interaction with immobilized analyte or interaction between analyte in the fluid test sample. Regardless of how the labeled antibodies are captured in the detection zone there will be a detectable response (absence of signal in the first case) which can be read by a properly programmed reflectance spectrometer. In various assays, the presence and/or the concentration of the analyte in the test sample is determined.

Many clinically significant target analytes are present in urine and are determinable by means of the type immunochromatographic strips contemplated herein. Among these analytes are deoxypyridinoline, human serum albumin and drugs of abuse such as amphetamines, barbiturates and cocaine. While the means for detecting the signal from the developed strip of the device of the present invention will depend on the detectable label attached to the labeled binding partner, the use of a reflectance spectrometer is typical when the label's detectable physical property is the reflectance of light at a predetermined wavelength. According to one embodiment of the present invention, there is provided a reflectance meter with means for moving the cassette containing the strip or the meter's detector element relative to each other such as by use of a specimen table for the strip which can be moved laterally under the readhead of the detector. As previously discussed, maintenance of careful temperature control increases the accuracy of the assay.

While the depicted embodiments of the fixture plate 26 and the cassette bottom 14 show two pairs of two fins 28, corresponding to two slots, respectively, various other configurations are available in alternative embodiments of the present invention. For example, the cassette bottom 14 may contain four narrow slots corresponding to each of the fins. Alternatively, the fixture plate 26 may contain a plurality of cylindrical shaped fins (e.g., rods), which protrude through circular holes in the cassette bottom 14 to provide temperature control on the temperate in the hollowing The cassette 10 is intended to be a disposable testing device. Having a disposable cassette 10 prevents or reduces the risk of contamination of the test area and the test sample. As discussed above, the cassette top 12 and bottom 14 arc made of plastic. The cassette top 12 and bottom 14 can be inexpensively manufactured by injection molding the top 12 and bottom 14 out of plastic including high impact polystyrene, ABS, or styrene according to alternative embodiments of the present invention. According to one embodiment of the present invention, the cassette bottom 14 includes a wall (not shown) made of a thin plastic material to prevent physical contact between the test sample and the fins 28. In such an embodiment, the thin wall prevents or reduces the risk of cross-contamination of subsequent test samples.

Figure 5:
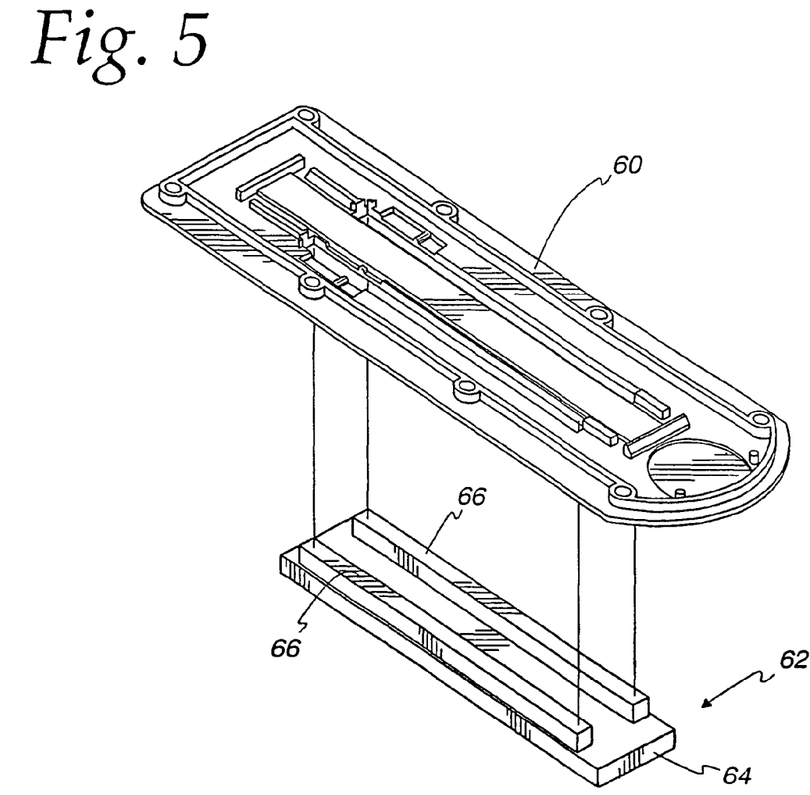
FIG. 5 is a perspective view of a cassette bottom and a heating mechanism according to an alternative embodiment of the present invention.
Figure 6:
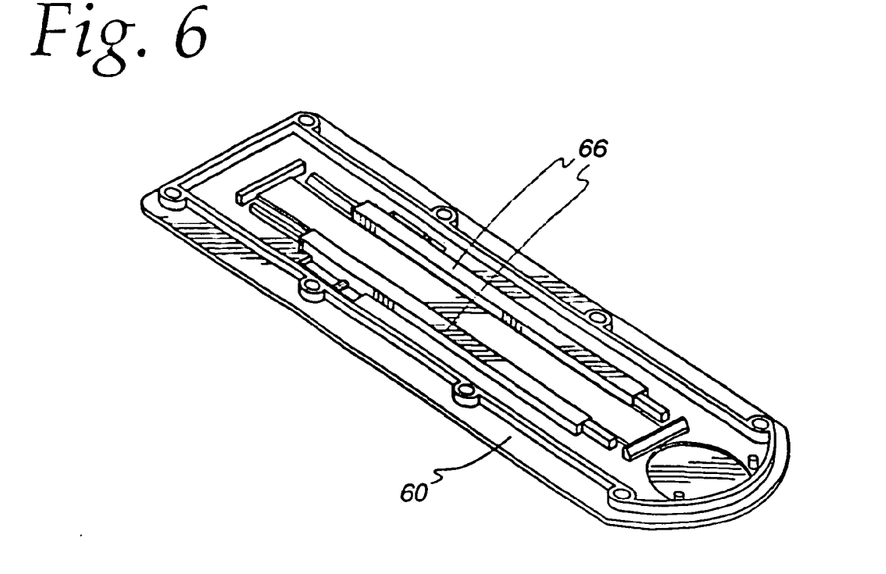
FIG. 6 is a perspective view of a cassette bottom upon the heating mechanism shown in FIG. 5.

Referring now to FIGS. 5 and 6, an alternative embodiment of a cassette bottom 60 and heating mechanism 62 is shown. The heating mechanism 62 includes a heater carrier 64 and resistive heating elements 66. The cassette bottom 60 is designed to mate with a cassette top similar to that shown FIG. 1. The cassette bottom illustrated in FIGS. 5 and 6 includes rectangular shaped apertures 68 for receiving the resistive heating elements 66. The resistive heating elements 66 protrude through the apertures 68 and into the hollow test chamber of the cassette when the cassette top (shown in FIG. 1) and the cassette bottom are mated. The cassette bottom 60 depicted in FIGS. 5 and 6 is similar to that shown in FIG. 14, except that the rectangular shaped apertures 68 may be sized differently than shown in FIGS. 1-4 depending on the physical size of the resistive heater elements.

When an assay is conducted, the heating mechanism 62 provides the advantage of quick temperature control as the resistive heating elements 66 rapidly heat up and, in turn, are able to quickly bring the hollow test chamber of the cassette to the desired temperature. Further, less time is required to bring the test chamber to the desired temperature because the heat source (i.e., the resistive heating elements 66) are brought into very close proximity to the test strip.

According to one embodiment of the present invention, a device such as the temperature control mechanism 30 illustrated in FIG. 4 may be used with the heating mechanism 62 illustrated in FIG. 5. The heating mechanism 62 replaces the fixture plate 26 having integral fins 28. The temperate control mechanism operates in a manner similar to that described in connection with FIG. 4. The temperature control mechanism contains circuitry designed to regulate the temperature inside the cassette by controlling the amount of current that passes through the resistive heating elements. According to an alternative embodiment, the heating mechanism 62 includes covers (not shown) disposed over the resistive heating elements 66 to prevent the resistive heating elements 66 from contacting the test strip during the assay.

Figures 7, 8, 9:
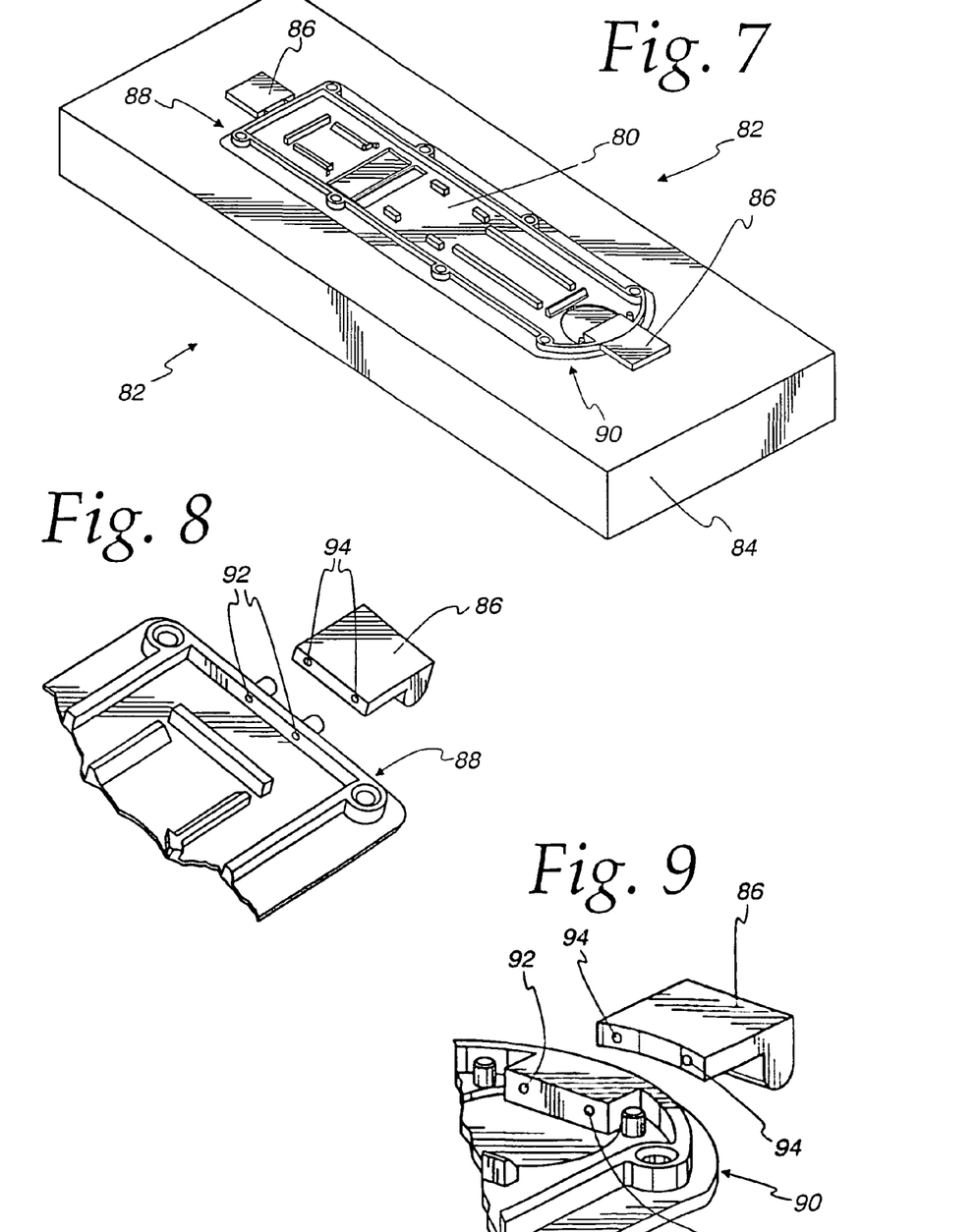
FIG. 7 is a perspective view of a cassette bottom inserted into a heating mechanism according to another alternative embodiment of the present invention.
FIGS. 8 and 9 are perspective views of opposite ends of the cassette bottom and corresponding hot air blowers according to the embodiment of the present invention shown in FIG. 7.

Referring now to FIGS. 7, 8, and 9, another alternative embodiment of a cassette bottom 80 and a heating mechanism 82 is shown. The cassette bottom 80 is shown inserted into the heating mechanism 82. The cassette bottom 80 is designed to mate with a cassette top similar to that shown in FIG. 1. The heating mechanism 82 includes a cassette carrier 84 and hot air blowers 86 disposed towards opposite ends 88, 90 of the cassette bottom 80. As shown best in FIGS. 8 and 9, each end 88, 90 of the cassette bottom 80 contains hot air inlet apertures 92 which correspond to outlets 94 of the hot air blowers 86. Each of the hot air blowers 86 includes a fan (not shown) which forces air over resistive heating elements (not shown) to produce a flow of hot air that exits the hot air blowers 86 through the outlet apertures 94.

The amount of heating provided by each of the hot air blowers 86 can vary according to the amount of current supplied to the resistive heating elements and the speed and size of the fan. Depending on the quantity of hot air produced by the hot air blowers 86, the heating mechanism 82 can quickly heat the air in the test chamber of the test cassette to the desired temperature. The heating mechanism 82 includes an electric circuit (not shown) that is designed to control the required temperature inside the cassette 80 by controlling the amount of current supplied to the resistive heating elements and the speed of the fan.

In conducting an assay, the test sample is applied to a test strip disposed in a test cassette via the cassette application port. The test cassette is inserted into the heating mechanism 82 and the hot air blowers 86 are turned on. According to one embodiment of the heating mechanism 82, the cassette carrier 84 contains a switch (not shown) so that when the test cassette is inserted into the cassette carrier 84, the hot air blowers are automatically turned on. Hot air is blown into the test chamber of the test cassette to raise the temperate of the test cassette to the desired level and then to maintain the test chamber at that temperature. According to an alternative embodiment, the test cassette bottom 80 contains appropriate baffle plates and channels to avoid direct flow of the heated air over the test strip so that evaporation of the test fluid is minimized. Additionally, according to one embodiment of the present invention, the cassette bottom includes one or more apertures allowing air to vent from the cassette bottom 80 while the test chamber is being filled with hot air from the hot air blowers 86.

While the invention is susceptible to various modifications and alternative forms, specific embodiments thereof have been shown by way of example in the drawings and herein described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

What is claimed is:

1. A device for evaluating at least one analyte in a test sample, the device comprising:
    a disposable cassette having a hollow test chamber and at least one aperture extending from an exterior of the cassette to the hollow test chamber;
    a test strip disposed within the test chamber for receiving the test sample, the test strip including a reagent for reacting with the at least one analyte to produce a reaction indicative of the presence of the analyte; and
    a temperature control member comprising at least one fin positioned adjacent to, but not in direct contact with, said test strip and extending through the at least one aperture in the cassette and into the test chamber for controlling the temperature of the test chamber, and a thermoelectric temperature control unit in thermal communication with the at least one fin for controlling the temperature of the test chamber.

2. The device of claim 1 wherein the test strip comprises an immunochromatographic test strip.

3. The device of claim 1 wherein the test strip is made out of a bibulous material.

4. The device of claim 1 wherein the cassette top and the cassette bottom are made of plastic.

5. The device of claim 1 wherein the at least one fin comprises a plurality of fins, and wherein the at least one aperture of the cassette comprises a plurality of apertures, each of the plurality of apertures for receiving one or more of the plurality of fins, one or more of the plurality of fins extending through each of the plurality of apertures into the test chamber.

6. The device of claim 5 wherein the temperature control member further comprises a fixture plate attached to the plurality of fins, and wherein the fixture plate and the plurality of fins are integrally formed.

7. The device of claim 6 wherein the fixture plate and the plurality of fins are made out of a thermally conductive material.

8. The device of claim 7 wherein the thermally conductive material is aluminum.

9. The device of claim 1 in combination with a spectrometer for reading the reaction indicative of the presence of the analyte.

10. An apparatus for controlling the temperature of an assay test strip, the apparatus comprising:
    a cassette carrier for receiving a disposable test cassette having at least one aperture;
    a thermally conductive member extending through the at least one aperture of a test cassette received by the cassette carrier and positioned adjacent to, but not in direct contact with, said test strip; and
    a temperature control unit in thermal communication with the thermally conductive member for controlling the temperature of said cassette carrier.

11. The apparatus of claim 10 wherein the thermally conductive member is made of aluminum.

12. The apparatus of claim 10 wherein the thermally conductive member comprises at least one fin fixedly attached to a fixture plate.

13. The apparatus of claim 12 wherein the fixture plate and at least one fin are integrally formed.

14. The apparatus of claim 12 wherein the at least one fin comprises two or more fins.

15. The apparatus of claim 12 wherein the material is a thermally conductive material.

16. The apparatus of claim 12 wherein the temperature control unit comprises a thermoelectric device.

17. The apparatus of claim 16 wherein the thermoelectric device is a Peltier Effect thermoelectric device.

18. A method for evaluating at least one analyte in a test sample, the method comprising:
providing a disposable test cassette having at least one aperture;
disposing a test strip within a test chamber of the test cassette, the test strip including a reagent for reacting with the at least one analyte to produce a reaction indicative of the presence of the analyte;
applying the test sample to the test strip;
controlling the temperature of the test chamber with a temperature control member in thermal communication with a thermoelectric temperature control unit extending through the at least one aperture formed in the test cassette, said temperature control member comprising at least one fin positioned adjacent to, but not in direct contact with, said test strip; and
evaluating said analyte in said test sample by reading said reaction indicative of said analyte.

19. The method of claim 18 further comprising detecting any change in the test strip.

20. The method of claim 18 wherein the test strip comprises an immunochromatographic test strip.

21. The method of claim 18 further comprising forming the test cassette from a cassette top and a cassette bottom.

22. The method of claim 18 wherein the temperature control member includes a fixture plate attached to the at least one fin, and wherein the fixture plate and the at least one fin are integrally formed.

23. The method of claim 22 wherein the fixture plate and the at least one fin are made out of a thermally conductive material.

24. A device for evaluating at least one analyte is a test sample, the device comprising:
a disposable cassette having a hollow test chamber and at least one aperture extending from an exterior of the cassettes to the hollow test chamber;
a test strip disposed within the test chamber for receiving the test sample, the test strip including a reagent for reacting with the at least one analyte to produce a reaction indicative of the presence of the analyte; and
a temperature control member comprising at least one resistive heating element, said temperature control member controlling the temperature in said cassette by the current supplied to said at least one resistive heating element.

25. The device of claim 24 wherein the at least one resistive heating element comprises a plurality of resistive heating elements, and wherein the at least one aperture of the cassette comprises a plurality of apertures, each of the plurality of apertures receiving one or more of the plurality of resistive heating elements, one or more of the plurality of resistive heating elements extending through each of the plurality of apertures into the test chamber.

26. The device of claim 24 further comprising a circuit for controlling the amount of current supplied to the at least one resistive heating element.

27. A method for evaluating at least one analyte in a test sample, the method comprising:
providing a disposable test cassette having at least one aperture;
disposing a test strip within a test chamber of the test cassette, the test strip including a reagent for reacting with the at least one analyte to produce a reaction indicative of the presence of the analyte:
applying the test sample to the test strip;
controlling the temperature of the test chamber with a temperature control member extending through the at least aperture formed in the test cassette, said temperature control member including at least one resistive heating element, the temperature of said at least one resistive heating element controlled by current supplied to said at least one resistive heating element; and
evaluating said analyte in the test sample by reading said reaction indicative of said sample.

28. The method of claim 27 wherein controlling further comprises controlling the amount of electrical current that passes through the at least one resistive heating element.

* * * * *